United States Patent
Eicken et al.

(10) Patent No.: US 6,417,398 B1
(45) Date of Patent: Jul. 9, 2002

(54) BENZAMIDOXIM DERIVATIVES, INTERMEDIATE PRODUCTS AND METHODS FOR PREPARING THEM, AND THEIR USE AS FUNGICIDES

(75) Inventors: Karl Eicken, Wachenheim; Joachim Rheinheimer, Ludwigshafen; Frank Wetterich, Mutterstadt; Eberhard Ammermann, Heppenheim; Gisela Lorenz, Neustadt; Siegfried Strathmann, Limburgerhof, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/508,599
(22) PCT Filed: Sep. 5, 1998
(86) PCT No.: PCT/EP98/05618
§ 371 (c)(1),
(2), (4) Date: Mar. 14, 2000
(87) PCT Pub. No.: WO99/14188
PCT Pub. Date: Mar. 25, 1999

(30) Foreign Application Priority Data

Sep. 18, 1997 (DE) .......... 197 41 098
Dec. 3, 1997 (DE) .......... 197 53 520
Jan. 23, 1998 (DE) .......... 198 02 460

(51) Int. Cl.$^7$ .......... C07C 233/05; A01N 37/18
(52) U.S. Cl. .......... 564/182; 514/617; 564/124; 564/184
(58) Field of Search .......... 564/182, 184, 564/124; 514/617

(56) References Cited

U.S. PATENT DOCUMENTS 5,847,005 A    12/1998    Kasahara

FOREIGN PATENT DOCUMENTS

EP    805 148    11/1997
JP    2-6453    * 1/1990

OTHER PUBLICATIONS

Derwent Abst. 02006453, 1990.
Derwent Abst. 98 –225189, 1998.

* cited by examiner

Primary Examiner—Shailendra Kumar
(74) Attorney, Agent, or Firm—Keil & Weinkauf

(57) ABSTRACT

The invention concerns benzamidoxim derivatives of formula (I) in which the substituents have the following meanings: $R^1$ represents hydrogen or fluorine; $R^2$ represents $C_1$–$C_6$ phenyl-alkyl, bearing on the cyclic phenyl compound one or several substituents selected in the group comprising halogen, $C_1$–$C_4$ alkyl, $C_1$–$C_4$ alkyl halide, $C_1$–$C_4$ alkoxy or $C_1$–$C_4$ alkoxy halide, or $C_1$–$C_4$ thienyl-alkyl, optionally bearing one or several substituents selected in the group comprising halogen, $C_1$–$C_4$ alkyl, $C_1$–$C_4$ alkyl halide, $C_1$–$C_4$ alkoxy or $C_1$–$C_4$ alkoxy or $C_1$–$C_4$ alkoxy halide, or $C_1$–$C_4$ pyrazol-alkyl, optionally bearing one or several substituents selected in the group comprising halogen, $C_1$–$C_4$ alkyl, $C_1$–$C_4$ alkyl halide, $C_1$–$C_4$ alkoxy or $C_1$–$C_4$ alkoxy halide.

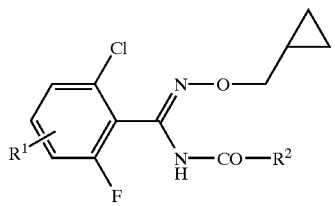

(I)

7 Claims, No Drawings

BENZAMIDOXIM DERIVATIVES, INTERMEDIATE PRODUCTS AND METHODS FOR PREPARING THEM, AND THEIR USE AS FUNGICIDES

This application is a 371 of PCT/EP98/05618, filed Sep. 5, 1998.

TECHNICAL FIELD

The present invention relates to novel benzamidoxime derivatives, to processes and intermediates for their preparation, and to their use as fungicides.

BACKGROUND ART

JP-A 02/006453 describes fungicidally active benzamidoxime derivatives which, however, are not entirely satisfactory, in particular when low rates of application are used.

It is an object of the present invention to provide novel benzamidoxime derivatives which have an improved activity, in particular even at low rates of application.

SUMMARY OF THE INVENTION

Surprisingly we have found that this object is achieved by benzamidoxime derivatives of the formula I

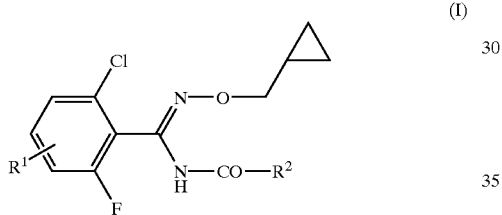

wherein
- $R^1$ is hydrogen or fluorine
- $R^2$ is phenyl-$C_1$-$C_6$-alkyl which may carry one or more substituents selected from the group consisting of halogen, $C_1$-$C_4$-alkyl, $C_1$-$C_4$-haloalkyl, $C_1$-$C_4$-alkoxy or $C_1$-$C_4$-haloalkoxy on the phenyl ring, or
- is thienyl-$C_1$-$C_4$-alkyl, which may carry one or more substituents selected from the group consisting of halogen, $C_1$-$C_4$-alkyl, $C_1$-$C_4$-haloalkyl, $C_1$-$C_4$-alkoxy or $C_1$-$C_4$-haloalkoxy, or
- is pyrazolyl-$C_1$-$C_4$-alkyl, which may carry one or more substituents selected from the group consisting of halogen, $C_1$-$C_4$-alkyl, $C_1$-$C_4$-haloalkyl, $C_1$-$C_4$-alkoxy or $C_1$-$C_4$-haloalkoxy.

In the definition of the substituents $R_1$ and $R_2$, the terms indicated are collective terms for a group of compounds.

Halogen is in each case fluorine, chlorine, bromine or iodine, in particular fluorine or chlorine.

Other meanings are, for example:

$C_1$-$C_4$-alkyl: methyl, ethyl, n-propyl, 1-methylethyl, n-butyl, 1-methylpropyl, 2-methylpropyl or 1,1-dimethylethyl, in particular methyl or ethyl;

$C_1$-$C_4$-haloalkyl: a $C_1$-$C_4$-alkyl radical as mentioned above, which is partially or fully substituted by fluorine, chlorine, bromine and/or iodine, i.e. for example chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-tri-chloroethyl, pentafluoroethyl, 2-fluoropropyl, 3-fluoro-propyl, 2,2-difluoropropyl, 2,3-difluoropropyl, 2-chloro-propyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoro-methyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl, in particular trifluoromethyl;

$C_1$-$C_4$-alkoxy: methoxy, ethoxy, n-propoxy, 1-methylethoxy, n-butoxy, 1-methylpropoxy, 2-methylpropoxy or 1,1-dimethyl-ethoxy, in particular methoxy or ethoxy;

$C_1$-$C_4$-haloalkoxy: a $C_1$-$C_4$-alkoxy radical as mentioned above, which is partially or fully substituted by fluorine, chlorine, bromine and/or iodine, i.e. for example chloro-methoxy, dichloromethoxy, trichloromethoxy, fluoromethoxy, difluoromethoxy, trifluoromethoxy, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoro-ethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromo-ethoxy, 4-fluorobutoxy, 4-chlorobutoxy, 4-bromobutoxy or nonafluorobutoxy, in particular difluoromethoxy;

phenyl-$C_1$-$C_6$-alkyl: for example benzyl, 1-phenylethyl, 2-phenylethyl, 1-phenylprop-1-yl, 2-phenylprop-1-yl, 3-phenylprop-1-yl, 1-(phenylmethyl)eth-1-yl, 1-(phenyl-methyl)-1-(methyl)eth-1-yl or 1-(phenylmethyl)prop-1-yl, in particular benzyl or 2-phenylethyl;

thienyl-$C_1$-$C_4$-alkyl: for example 2-thienylmethyl, 3-thienyl-methyl, 2-thienylethyl, 2-thienylprop-1-yl or 3-thienylprop-1-yl;

pyrazolyl-$C_1$-$C_4$-alkyl: for example 1-pyrazolylmethyl, 2-pyrazolylmethyl, 3-pyrazolylmethyl, 2-pyrazolylethyl, 2-pyrazolylprop-1-yl or 3-pyrazolylprop-1-yl, Compounds in which the substituent $R^2$ is benzyl which carries one to three substituents selected from the above-mentioned group on the phenyl ring, in particular one to three substituents selected from the group consisting of fluorine, chlorine, methyl, methoxy or trifluoromethyl, have generally proved especially effective. Particularly preferred substituents $R^2$ are 4-fluorobenzyl, 4-chlorobenzyl, 4-methylbenzyl, 4-methoxybenzyl, 4-trifluoromethylbenzyl and 4-difluoromethoxybenzyl.

Compounds of the formula I in which $R^1$ and $R^2$ have the meanings listed in Table 1 below are particularly preferred.

TABLE 1

| No. | R¹ | R² | m.p. (° C.) |
|---|---|---|---|
| I.1 | H | 4-CH₃—C₆H₄—CH₂ | 86–88 |
| I.2 | H | 4-F—C₆H₄—CH₂ | 79–81 |
| I.3 | H | 4-Cl—C₆H₄—CH₂ | 105–107 |
| I.4 | H | 4-CH₃O—C₆H₄—CH₂ | 73–76 |
| I.5 | H | 4-CF₃—C₆H₄—CH₂ |  |
| I.6 | 5-F | 4-CH₃—C₆H₄—CH₂ | 87–90 |
| I.7 | 5-F | 4-F—C₆H₄—CH₂ | 71–74 |
| I.8 | 5-F | 4-Cl—C₆H₄—CH₂ | 85–87 |
| I.9 | 5-F | 4-CH₃O—C₆H₄—CH₂ | 90–92 |
| I.10 | 5-F | 4-CF₃—C₆H₄—CH₂ |  |
| I.11 | H | 2-thienylmethyl | 87–89 |
| I.12 | H | 3-thienylmethyl |  |
| I.13 | 5-F | 2-thienylmethyl | 90–93 |
| I.14 | 5-F | 3-thienylmethyl |  |
| I.15 | 5-F | 3-CH₃—C₆H₄—CH₂ | 72–75 |
| I.16 | 5-F | 2-F—C₆H₄—CH₂ | 73–76 |
| I.17 | 5-F | 4-CH₂OF—C₆H₄—CH₂ | oil |

The benzamidoxime derivatives of the formula I according to the invention are obtained by the process according to the invention by means of the reaction of benzonitriles of the formula II with hydroxylamine or salts thereof in aqueous solution, preferably in (water or water/alkanol mixtures, if appropriate in the presence of a base, to give the benzamidoximes of the formula III which are subsequently reacted in a manner known per se in the presence of a base with cyclopropylmethyl halide to give the compounds of the formula IV.

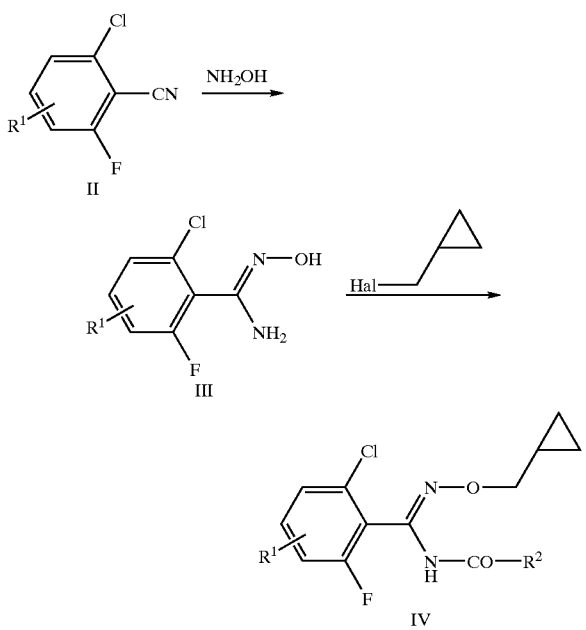

The benzamidoximes IV can then be acylated in a manner known per se with the appropriate acyl halides, preferably the appropriate acyl chlorides, by heating in inert solvents (preferably at from 20 to 100° C.).

Particularly suitable inert solvents are hydrocarbons or ethers, especially preferably aromatic hydrocarbons, such as toluene or xylene, to mention but two examples.

The intermediates of the formula III listed in the reaction scheme above in which R¹ is fluorine, and the intermediates of the formula IV are novel. Preferred compounds are those in which R¹ and R² have the meanings mentioned for the compounds I.

The compounds I are distinguished by an outstanding activity against a broad spectrum of phytopathogenic fungi, in particular from the classes of the Ascomycetes, Deuteromycetes, Phycomycetes and Basidiomycetes. Some of them act systemically, and they can therefore also be employed as foliar- and soil-acting fungicides.

Normally, the plants are sprayed or dusted with the active ingredients, or the seeds of the plants are treated with the active ingredients.

The formulations are prepared in a known manner, eg. by extending the active ingredient with solvents and/or carriers, if desired using emulsifiers and dispersants, it also being possible to use other organic solvents as auxiliary solvents if water is used as the diluent. Auxiliaries which are suitable are essentially: solvents such as aromatics (eg. xylene), chlorinated aromatics (eg. chlorobenzenes), paraffins (eg. mineral oil fractions), alcohols (eg. methanol, butanol), ketones (eg. cyclohexanone), amines (eg. ethanolamine, dimethylformamide) and water; carriers such as ground natural minerals (eg. kaolins, clays, talc, chalk) and ground synthetic minerals (eg. highly disperse silica, silicates); emulsifiers such as nonionic and anionic emulsifiers (eg. polyoxyethylene fatty alcohol ethers, alkylsulfonates and arylsulfonates) and dispersants such as lignin-sulfite waste liquors and methylcellulose.

Suitable surfactants are the alkali metal salts, alkaline earth metal salts and ammonium salts of aromatic sulfonic acids, eg. ligno-, phenol-, naphthalene- and dibutylnaphthalenesulfonic acid, and of fatty acids, alkylsulfonates, alkylarylsulfonates, alkyl sulfates, lauryl ether sulfates and fatty alcohol sulfates, and salts of sulfated hexa-, hepta- and octadecanols, and of fatty alcohol glycol ethers, condensates of sulfonated naphthalene and its derivatives with formaldehyde, condensates of naphthalene or of the naphthalenesulfonic acids with phenol or formaldehyde, polyoxyethylene octylphenol ether, ethoxylated iso-octylphenol, octylphenol or nonylphenol, alkylphenyl polyglycol ethers, tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors and methylcellulose.

Powders, materials for spreading and dusts can be prepared by mixing or concomitantly grinding the active substances with a solid carrier.

Granules, eg. coated granules, impregnated granules and homogeneous granules, can be prepared by binding the active ingredients to solid carriers. Examples of solid carriers are mineral earths, such as silicas, silica gels, silicates, talc, (a kaolin, limestone, lime, chalk, bole, loess, clay, dolomite, diatomaceous earth, calcium sulfate, magnesium sulfate, magnesium oxide, ground synthetic materials, fertilizers, eg. ammonium sulfate, ammonium phosphate, ammonium nitrate, ureas, and products of vegetable origin, such as cereal meal, tree bark meal, wood meal and nutshell meal, cellulose powders or other solid carriers.

The following are examples of such formulations:

I. a solution, suitable for use in the form of microdrops, of 90 parts by weight of a compound I according to the invention and 10 parts by weight of N-methyl-2-pyrrolidone;

II. a mixture of 10 parts by weight of a compound I according to the invention, 70 parts by weight of xylene, 10 parts by weight of the adduct of 8 to 10 mol of ethylene oxide to 1 mol of oleic acid N-monoethanolamide, 5 parts by weight of calcium dodecylbenzenesulfonate, 5 parts by weight of the adduct of 40 mol of ethylene oxide to 1 mol of castor oil; a dispersion is obtained by finely distributing the solution in water;

III. an aqueous dispersion of 10 parts by weight of a compound I according to the invention, 40 parts by weight of cyclohexanone, 30 parts by weight of isobutanol, 20 parts by weight of the adduct of 40 mol of ethylene oxide to 1 mol of castor oil;

IV. an aqueous dispersion of 10 parts by weight of a compound I according to the invention, 25 parts by weight of cyclohexanol, 55 parts by weight of a mineral oil fraction of boiling point 210 to 280° C. and 10 parts by weight of the adduct of 40 mol of ethylene oxide to 1 mol of castor oil;

V. a mixture, ground in a hammer mill, of 80 parts by weight, preferably of a solid compound I according to the invention, 3 parts by weight of sodium diisobutylnaphthalene-2-sulfonate, 10 parts by weight of the sodium salt of a lignosulfonic acid from a sulfite waste liquor and 7 parts by weight of pulverulent silica gel; a spray mixture is obtained by finely distributing the mixture in water;

VI. an intimate mixture of 3 parts by weight of a compound I according to the invention and 97 parts by weight of finely divided kaolin; this dust comprises 3% by weight of active ingredient;

VII. an intimate mixture of 30 parts by weight of a compound I according to the invention, 62 parts by weight of pulverulent silica gel and 8 parts by weight of paraffin oil which had been sprayed onto the surface of this silica gel; this formulation imparts good adhesion to the active ingredient;

VIII. a stable aqueous dispersion of 40 parts by weight of a compound I according to the invention, 10 parts by weight of the sodium salt of a phenolsulfonic acid/urea/formaldehyde condensate, 2 parts by weight of silica gel and 48 parts by weight of water; this dispersion can be diluted further;

IX. a stable oily dispersion of 20 parts by weight of a compound I according to the invention, 2 parts by weight of calcium dodecylbenzenesulfonate, 8 parts by weight of fatty alcohol polyglycol ether, 20 parts by weight of the sodium salt of a phenolsulfonic acid/urea/formaldehyde condensate and 50 parts by weight of a paraffinic mineral oil.

The novel compounds are distinguished by an outstanding activity against a broad spectrum of phytopathogenic fungi, in particular from the classes of the Deuteromycetes, Ascomycetes, Phycomycetes and Basidiomycetes. Some of them act systemically, and they can be employed as foliar- and soil-acting fungicides.

They are especially important for controlling a large number of fungi on a variety of crop plants such as wheat, rye, barley, oats, rice, maize, turf, cotton, soya, coffee, sugar cane, grapevines, fruit species, ornamentals and vegetables such as cucumbers, beans and cucurbits, and on the seeds of these plants.

The compounds are applied by treating the fungi, or the seeds, plants, materials or the soil to be protected against fungal infection, with a fungicidally active amount of the active ingredients.

Application can be effected both before and after infection of the materials, plants or seeds by the fungi.

Specifically, the novel compounds are suitable for controlling the following plant diseases:

Erysiphe graminis (powdery mildew) in cereals, Erysiphe cichoracearum and Sphaerotheca fuliginea on cucurbits, Podosphaera leucotricha on apples, Uncinula necator on grapevines, Puccinia species on cereals, Rhizoctonia species on cotton and turf, Ustilago species on cereals and sugar cane, Venturia inaequalis (scab) on apples, Helminthosporium species on cereals, Septoria nodorum on wheat, Botrytis cinerea (gray mold) on strawberries, grapevines, ornamentals and vegetables, Cercospora arachidicola on peanuts, Pseudocercosporella herpotrichoides on wheat, barley, Pyricularia oryzae on rice, Phytophthora infestans on potatoes and tomatoes, Fusarium and Verticillium species on a variety of plants, Plasmopara viticola on grapevines and Alternaria species on vegetables and fruit.

The novel compounds can also be employed in the protection of materials (protection of wood), for example against Paecilomyces variotii.

In general, the fungicidal compositions comprise from 0.1 to 95, preferably from 0.5 to 90, % by weight of active ingredient.

Depending on the nature of the desired effect, the rates of application are from 0.025 to 2, preferably 0.1 to 1, kg of active ingredient per ha.

In the treatment of seed, amounts of from 0.001 to 50, preferably 0.01 to 10, g of active ingredient are generally required per kilogram of seed.

In the use form as fungicides, the agents according to the invention can also be present together with other active ingredients, eg. with herbicides, insecticides, growth regulators, fungicides or else with fertilizers.

Mixing with fungicides frequently results in a broader fungicidal spectrum of action.

The following list of fungicides together with which the compounds according to the invention can be used is intended to illustrate the possible combinations, but not to impose any limitation:

sulfur, dithiocarbamates and their derivatives, such as iron(III) dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfide, ammonia complex of zinc (N,N-ethylenebisdithiocarbamate), ammonia complex of zinc (N,N'-propylenebisdithiocarbamate), zinc (N,N'-propylenebisdithiocarbamate), N,N'-polypropylenebis (thiocarbamoyldisulfide;

nitro derivatives, such as dinitro-(1-methylheptyl)phenyl crotonate, 2-sec-butyl-4,6-dinitrophenyl 3,3-dimethylacrylate, 2-secbutyl-4,6-dinitrophenylisopropyl carbonate, diisopropyl 5-nitroisophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-[bis-(dimethylamino)phosphinyl]-3-phenyl-1,2,4-triazole, 2,3-dicyano-1,4-dithioanthraquinone, 2-thio-1,3-dithiolo[4,5-b] quinoxaline, methyl 1-(butylcarbamoyl)-2-benzimidazolecarbamate, 2-methoxycarbonylaminobenzimidazole, 2-(2-furyl)benzimidazole, 2-(4-thiazolyl)benzimidazole, N-(1,1,2,2-tetrachloroethylthio)tetrahydrophthalimide, N-trichloromethylthiotetrahydrophthalimide, N-trichloromethylthiophthalimide;

N-dichlorofluoromethylthio-N',N'-dimethyl-N-phenylsulfodiamide, 5-ethoxy-3-trichloromethyl-1,2,3- thiadiazole, 2-thiocyanatomethylthiobenzothiazole, 1,4-dichloro-2,5-dimethoxybenzene, 4-(2-chlorophenylhydrazono)-3-methyl-5-isoxazolone, pyridine-2-thione 1-oxide, 8-hydroxyquinoline or its copper salt, 2,3-dihydro-5-carboxanilido-6-methyl-1,4-oxathiine, 2,3-dihydro-5-carboxanilido-6-methyl-1,4-oxathiine 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethyl-furan-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine-2,2,2-trichloroethyl acetal, piperazine-1,4-diylbis-1-(2,2,2-trichloroethyl)formamide, 1-(3,4-dichloroanilino)-1-formylamino-2,2,2-trichloroethane;

2,6-dimethyl-N-tridecyl-morpholine or its salts, 2,6-dimethyl-N-cyclododecylmorpholine or its salts, N-[3-(p-tert-butylphenyl)-2-methylpropyl]cis-2,6-dimethylmorpholine, N-[3-(p-tert-butylphenyl)-2-methyl-propyl]piperidine, 1-[2-(2,4-dichlorophenyl)-4-ethyl-1,3-dioxolan-2-ylethyl]-1H-1,2,4-triazole, 1-[2-(2,4-dichlorophenyl)-4-n-propyl-1,3-dioxolan-2-ylethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)- 2-butanone, (2-chlorophenyl) (4-chlorophenyl)-5-pyrimidine-methanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)benzene, [2-(4-chlorophenyl) ethyl]-(1,1-dimethylethyl)-1H-1,2,4-triazol-1-ethanol, 1-[3-(2-chlorophenyl)-1-(4-fluoro-phenyl)oxiran-2-ylmethyl]-1H-1,2,4-triazole, and a variety of fungicides such as dodecylguanidine acetate, 3-[3-(3,5-dimethyl-2-oxycyclohexyl)-2-hydroxyethy] glutarimide, hexachlorobenzene, methyl N-(2,6-dimethylphenyl)-N-(2-furoyl)-DL-alaninate, DL-N-(2,6-dimethylphenyl)-N-(2'-methoxyacetyl)-alanine methyl ester, N-(2,6-dimethylphenyl)-N-chloroacetyl-D,L-2-aminobutyrolactone, DL-N-(2,6-dimethylphenyl)-N-(phenylacetyl)alanine methyl ester, 5-methyl-5-vinyl-3-(3,5-dichlorophenyl)-2,4-dioxo-1,3-oxazolidine, 3-(3,5-dichlorophenyl)-5-methyl-5-methoxymethyl-1,3-oxazolidine-2,4-dione, 3-(3,5-dichlorophenyl)-1-isopropyl-carbamoylhydantoin, N-(3,5-dichlorophenyl)-1,2-dimethylcyclo-propane-1,2-dicarboximide, 2-cyano-[N-(ethylaminocarbonyl)-2-methoximino]acetamide, 1-[2-(2,4-dichlorophenyl)-pentyl]-1H-1,2,4-triazole, 2,4-difluoro-α-(1H-1,2,4-triazolyl-1-methyl)benzhydryl alcohol, N-(3-chloro-2,6-dinitro- 4-trifluoromethylphenyl)-5-trifluoromethyl-3-chloro-2-aminopyridine, 1-((bis(4-fluorophenyl) methylsilyl)methyl)-1H-1,2,4-triazole, strobilurins such as methyl E-methoximino-[α-(o-tolyloxy)- o-tolyl]acetate, methyl E-2-{2-[6-(2-cyanophenoxy)pyridimin-4-yloxy]phenyl}-3-methoxyacrylate, N-methyl- E-methoximi-no-[α-(2,5-dimethyloxy)-o-tolyl]acetamide, anilinopyrimidines such as N-(4,6-dimethylpyrimidin-2-yl)aniline, N-[4-methyl-6-(1-propynyl)pyrimidin-2-yl] aniline, N-(4-methyl-6-cyclopropylpyrimidin-2-yl) aniline, phenylpyrroles such as 4-(2,2-difluoro-1,3-benzodioxol-4-yl)pyrrole-3-carbonitrile, cinnamamides such as 3-(4-chlorophenyl)-3-(3,4-dimethoxyphenyl)acryloylmorpholine.

EXAMPLE

Example 1 a) 2-Chloro-6-fluorobenzamidoxime

A mixture of 15.6 g of 2-chloro-6-fluorobenzonitrile, 9.0 g of hydroxylamine hydrochloride, 7.4 g of sodium carbonate, 50 ml of ethanol and 15 ml of water was stirred at 70–75° C. for 16 h. The solvent was evaporated and the residue was stirred with tertbutyl methyl ether, and the filtrate afforded, after evaporation of the solvent, 17.6 g of the desired product of m.p. 115–120° C.

b) 2–Chloro-6-fluorobenzamide [o-cyclopropylmethyl] oxime

At 0° C., 0.3 g of sodium hydride (80% pure) were added a little at a time over a period of 15 minutes to a mixture of 1.9 g of the product obtained under a) and 1.6 g of cyclopropylmethyl bromide in 20 ml of dimethylformamide, and the mixture was stirred at 5° C. for 3 h. The batch was stirred into water and extracted three times with 70 ml of cyclohexane each time. The cyclohexane was evaporated and 1.9 g of the desired product were isolated as an oil.

NMR(CDCl$_3$) in ppm: 0.3 m (2H); 0.50 m (2H); 1.2 m (1H); 3.9 d (2H); 4.8 s,br (2H); 6.95–7.10 m (1H); 7.2–7.3 m (2H).

c) N-Phenylacetyl-2-chloro-6-fluorobenzamide [O-cyclopropyl-methyl]oxime 1.2 g of the product obtained by method b) and 1.1 g of phenylacetyl chloride in 40 ml of toluene were heated at reflux for 7 h. After cooling, 40 ml of water were added and the pH was adjusted to 11. The toluene phase gave, after evaporation of the solvent, 1.6 g of a crystalline crude product which, after recrystallization, afforded 0.7 g of the desired product of m.p. 79–81° C.

NMR(CDCl$_3$) in ppm: 0.2 m (2H); 0.5 m (2H); 1.05 m (1H); 3.65 s (2H); 4.9 d (2H); 6.9–7.05 m (1H); 7.2–7.4 m (7H); 8.5 s,br(1H).

In a similar manner to that described in Example 1, the following products of the formulae III and IV were prepared.
Formula III: 2-chloro-5,6-difluorobenzamidoxime
Formula IV: 2-chloro-5,6-difluorobenzamide [O-cyclopropyl-methyl]oxime NMR(CDCl$_3$) in ppm: 0.3 m (2H); 0.55 m (2H); 1.4 m (1H); 3.9 d (2H); 4.85 s,br (2H); 7.1–7.2 m (2H).

The benzamidoxime derivatives of the formula I prepared in this manner are shown in Table 2.

TABLE 2

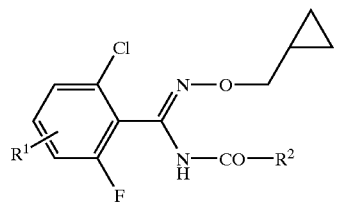

(I)

| No. | R$^1$ | R$^2$ | m.p. (° C.) |
|---|---|---|---|
| II.1 | H | C$_6$H$_5$—CH$_2$ | 79–81 |
| II.2 | 5-F | C$_6$H$_5$—CH$_2$ | 90–92 |
| II.3 | H | 3-thienylmethyl | 78–80 |

Example 2

Activity against powdery mildew of wheat

Leaves of potted wheat seedlings c.v. "Frühgold" were sprayed to runoff point with an aqueous preparation of active ingredient made with a stock solution comprising 10% of active ingredient, 63% of cyclohexanone and 27% of emulsifier and, 24 hours after the spray coating had dried on, dusted with spores of powdery mildew of wheat (Erysiphe graminis f.sp.tritici). The test plants were subsequently placed in a greenhouse at from 20 to 22° C. and a relative atmospheric humidity of 75 to 80%. After 7 days, the extent of the mildew development was determined visually in % of the total leaf area.

The disease level of the plants which had been treated with the active ingredients I.1, I.2, I.4 and I.11 of Table 1 was 15% at most, the plants which had been treated with the active ingredients II.1 and II.3 of Table 2 were free from disease, while the disease level of the untreated plants was 80%.

We claim:

1. A benzamidoxime of formula I

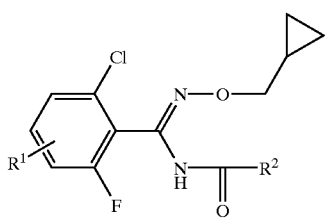

(I)

where:
  $R^1$ is hydrogen or fluorine,
  $R^2$ is phenyl-$C_1$–$C_6$-alkyl which is unsubstituted or carries one or more substituents selected from the group consisting of halogen, $C_1$–$C_4$-alkyl, $C_1$–$C_4$-haloalkyl, $C_1$–$C_4$-alkoxy and $C_1$–$C_4$-haloalkoxy on the phenyl ring.

2. The benzamidoxime of formula I as claimed in claim 1, in which $R^1$ is hydrogen.

3. The benzamidoxime of formula I as claimed in claim 1, in which $R^1$ is fluorine which is in the 5-position of the phenyl ring.

4. The benzamidoxime of formula I as claimed in claim 1, in which $R^2$ is benzyl which carries one to three substituents selected from the group consisting of fluorine, chlorine, methyl, methoxy and trifluoromethyl on the phenyl ring.

5. A process for preparing the benzamidoxime of formula I as claimed in claim 1, which comprises reacting a benzonitrile of formula II

(II)

with hydroxylamine or a salt thereof in aqueous solution, to give a benzamidoxime of formula III

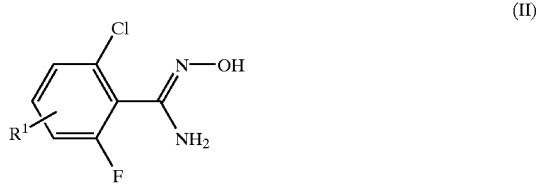

(II)

($R^1$=H or F), subsequently reacting the benzamidoxime of formula III with a cyclopropylmethyl halide to give a benzamidoxime of formula IV

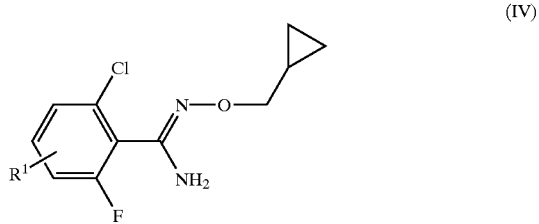

(IV)

and reacting the benzamidoxime of formula IV with an acyl halid to give the benzamidoxime of formula I.

6. A composition having fungicidal action, comprising at least one benzamidoxime of formula I as claimed in claim 1.

7. A method for controlling harmful fungi, which comprises treating the harmful fungi, their habitat or plants, areas, materials or spaces to be kept free from them with a compound of formula I as claimed in claim 1 or with a composition comprising a benzamidoxime of formula I.

* * * * *